United States Patent

DeFiore

Patent Number: 5,181,274
Date of Patent: Jan. 26, 1993

[54] CATHERER SHOWER SHIELD

[76] Inventor: Hannah B. DeFiore, 18665 Midway, #2412, Dallas, Tex. 75287

[21] Appl. No.: 741,681

[22] Filed: Aug. 7, 1991

[51] Int. Cl.⁵ .......................................... A41D 13/00
[52] U.S. Cl. .................................. 2/46; 2/48; 2/49 R; 2/DIG. 7; 128/887; 128/888; 604/162; 604/163; 604/192
[58] Field of Search ............... 2/2, 46, 48, 49 R, 50, 2/51, 52, 114, 174, DIG. 7; 128/887, 888; 604/162, 163, 192, 197

[56] References Cited

U.S. PATENT DOCUMENTS

| | | | |
|---|---|---|---|
| 720,812 | 2/1903 | Johnson | 128/888 |
| 1,319,299 | 10/1919 | Meehan | 128/888 |
| 1,376,625 | 5/1921 | Johnston | 2/49 R |
| 2,420,916 | 5/1947 | Sorge . | |
| 2,436,547 | 2/1948 | Boccieri | 2/49 R |
| 3,265,065 | 8/1966 | Jillson | 2/DIG. 7 X |
| 3,557,385 | 1/1971 | Hendrickson | 2/114 |
| 3,868,728 | 3/1975 | Krzewinski | 2/114 |
| 4,000,737 | 1/1977 | Horn | 128/888 |
| 4,133,052 | 1/1979 | Hodgman et al. . | |
| 4,578,062 | 3/1986 | Schneider | 2/DIG. 7 X |
| 4,582,508 | 4/1986 | Pavelka | 2/DIG. 7 X |
| 4,891,846 | 1/1990 | Sager et al. | 128/888 X |
| 4,975,982 | 12/1990 | Hughes . | |
| 5,048,122 | 9/1991 | Prieur | 2/DIG. 7 X |

Primary Examiner—Werner H. Schroeder
Assistant Examiner—Jeanette E. Chapman
Attorney, Agent, or Firm—Daniel V. Thompson

[57] ABSTRACT

A shield for protecting a catheter while a patient is taking a shower/bath includes a first band for engaging a first portion of the patient's body and having an intermediate portion, a second band for engaging a second portion of the patient's body and having an intermediate portion, a water proof panel spanning between the intermediate portions of the bands, and water absorbent panels on lateral sides of the water proof panel and spanning between the intermediate portions of the bands.

3 Claims, 1 Drawing Sheet

CATHERER SHOWER SHIELD

TECHNICAL FIELD

This invention relates to medical devices, and more particularly to a protective device to be worn while a patient takes a shower bath to protect a catheter.

BACKGROUND ART

Cancer is one of the most dreaded words in medicine but is also becoming increasingly controlled and treated with a variety of surgical, chemical and irradiation processes. The early detection of most cancers through improved testing and screening processes has made early intervention and complete cures possible in cancers which once were invariably fatal.

Among women, cancer of the breast is the most common form of the disease and has traditionally been detectable and treatable through removal of the breast alone or the breast and surrounding tissue and glands. This process requires additional radiation or chemical therapy to ensure complete destruction of all malignant cells.

Increasingly, breast cancer is being detected in early stages through routine mammograms. Detection at such early stages greatly reduces the volume of malignant cell mass to be removed.

The one aspect that has not changed is the need for chemotherapy to reinforce the surgical excision. Such chemotherapy is often introduced through a catheter placed between the breasts to distribute the chemicals directly to the action site for efficient action and reduced side affects.

The catheter must remain in place until the therapy is completed, and during this time the insertion site must be protected from water. Such protection precludes normal showering that can frustrate the individual and complicate personal hygiene and grooming.

Thus, there presently exists a need for a device that would cover the catheter site to allow breast cancer patients to shower normally without risk.

SUMMARY OF THE INVENTION

The present invention is a shield for protecting a catheter while a patient is taking a shower bath. In the preferred embodiment, the shield fits like a bib around the neck and chest to keep the catheter site dry, while allowing the rest of the body to be soaped, shampooed and rinsed for comfort, hygiene and grooming. Preferably, the shield includes a waterproof panel that spans between bands that engage the patient's body, with water absorbent panels on the lateral sides of the waterproof panel to prevent infiltration of water to the catheter site.

BRIEF DESCRIPTION OF THE DRAWING

A more complete understanding of the invention and its advantages will be apparent from the Detailed Description taken in conjunction with the accompanying Drawings in which.

DETAILED DESCRIPTION OF THE PREFERRED EMBODIMENT

Figure 1:
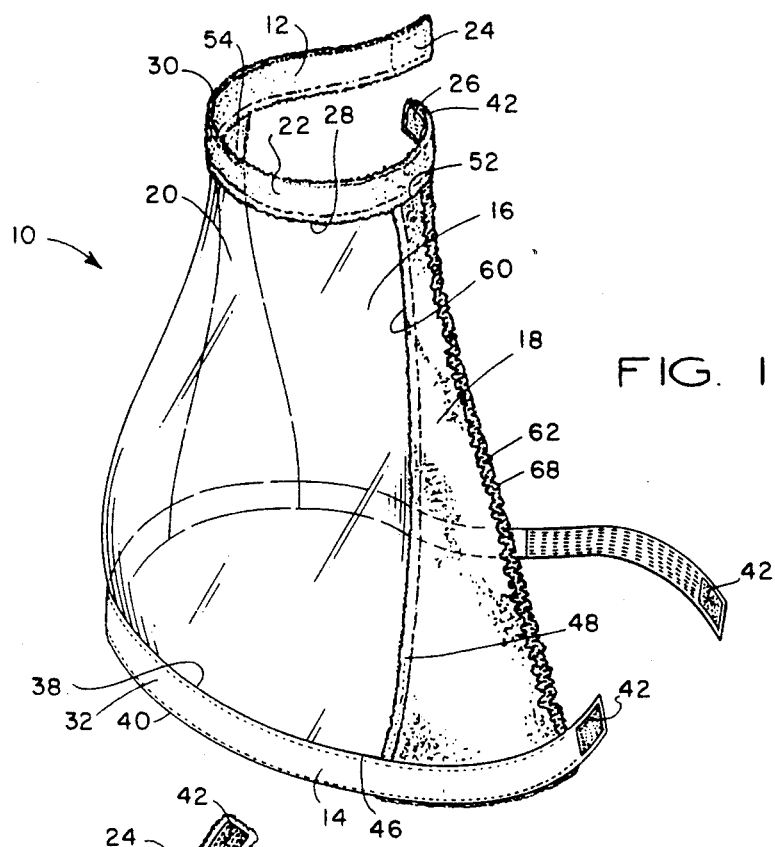
FIG. 1 is a perspective view of a shield constructed in accordance with the invention.
Figure 2:
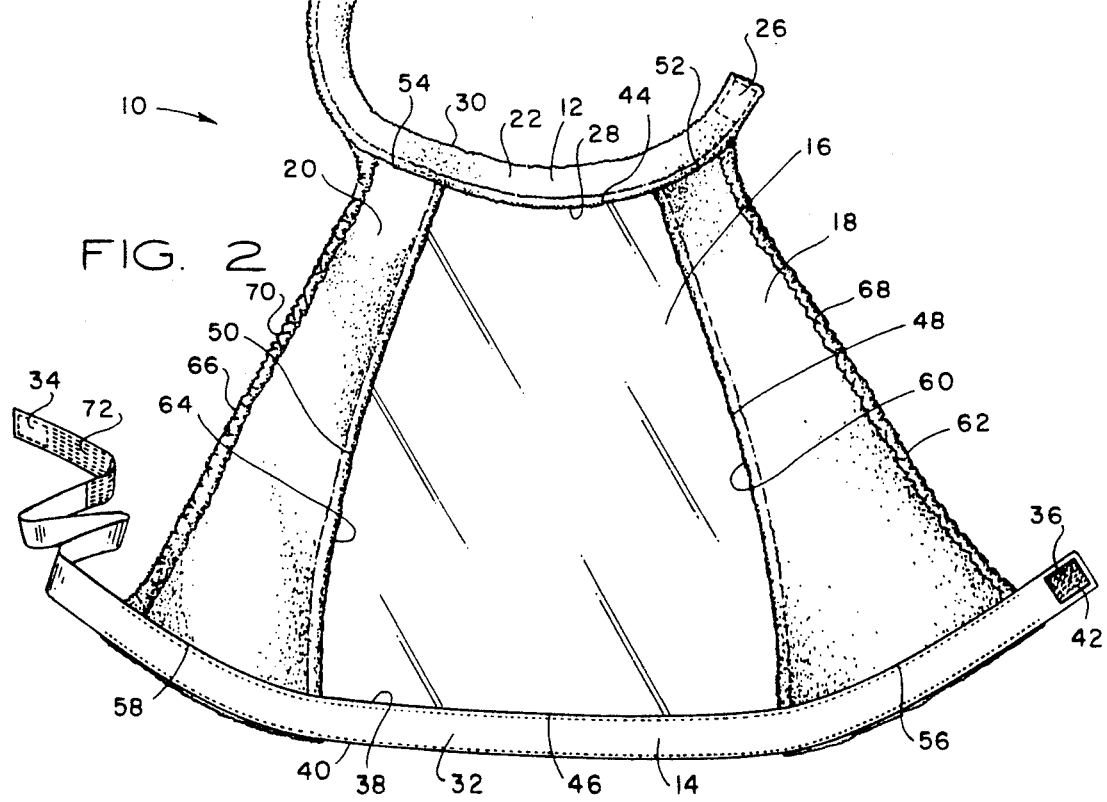
FIG. 2 is a view of the shield of FIG. 1 spread approximately flat.

Referring to FIGS. 1 and 2, shield 10 includes a first band 12, a second band 14, a waterproof panel 16, and two water absorbent panels 18 and 20. First band 12 is constructed and arranged to engage the patient's neck, and has an intermediate portion 22 between two ends 24 and 26. Intermediate portion 12 has two lateral edges 28 and 30.

Second band 14 is constructed and arranged to engage the patient's chest, and has an intermediate portion 32 between two ends 34 and 36. Intermediate portion 32 has two lateral edges 38 and 40. Loop fasteners 42 are connected to ends 24, 26, 34 and 36.

Waterproof panel 16 has an upper edge 44, a lower edge 46 and two lateral edges 48 and 50. Waterproof panel 16 spans between intermediate portions 22 and 32 of bands 12 and 14, respectively, with upper edge 44 attached to first and intermediate portion lateral edge 28. Lower edge 46 of waterproof panel 16 is attached to lateral edge 38 of second band intermediate portion 32. The other intermediate portion lateral edges, edges 30 and 40, are free edges, meaning that they are not attached to any other portion of the device and form a portion of the perimeter of shield 10.

Water absorbent panels 18 and 20 are on the lateral sides of waterproof panel 16, i.e., the sides of waterproof panel 16 that are not connected to first and second bands 12 and 14. Each water absorbent panel has upper edges 52, 54, lower edges 56, 58 and two lateral edges 60, 62, 64 and 66. Water absorbent panels 18 and 20 span between intermediate portions 22 and 32 of bands 12 and 14, respectively. Upper edges 52 and 54 are attached to lateral edge 28 of intermediate portion 22. Lower edges 56 and 58 are attached to lateral edge 38 of second band intermediate portion 32. Lateral edge 60 is attached to lateral edge 48, and lateral edge 64 is attached to lateral edge 50. Lateral edges 62 and 66 are free edges. Elastic is sewn within pockets 68 and 70 sewn into lateral edges 62 and 66 respectively. It thus can be seen that waterproof panel 16 is bounded on all sides by the band intermediate portions 22, 32 and the water absorbent panels 18, 20. Band 14 includes an elastic portion 72.

The preferred embodiment of the invention uses a soft, woven terry cloth or similar fabric to form water absorbent panels 18, 20 and bands 12, 14. A textured, sheet, plastic material is used for waterproof panel 16. Band 12 is approximately one inch wide and 16 inches long, so that it is constructed and arranged to attach around the patient's neck. The shield assembly composed of waterproof panel 16 with water absorbent panels 18, 20 at its sides is roughly triangular in shape, flaring to an approximately 15 inch width at the base. Band 14 is formed of a nonelastic poplin or broad cloth material. Band 14 is constructed and arranged to enable the anchoring of the shield 10 about the patient's torso. Waterproof panel 16 in the preferred embodiment is approximately six inches wide along upper edge 44 and 12 inches wide along lower edge 46. Lateral edges 48, 50 are approximately 14 inches in length, as are lateral edges 60, 62, 64 and 66. Second band 14 is approximately one inch wide and approximately 40 inches long, with elastic portion 72 being approximately six inches of the total length. The elastic lateral edges 68 and 70 are approximately one-half inch wide to provide a comfortable fabric margin of the shield.

Assembly of the shield 10 will be according to conventional sewing practices. Assembly will begin with the design of patterns for the various pieces, with seam allowances calculated to allow assembly to a pre-determined size. The pattern will be placed over multiple layers of material spread either by hand or machine on tables and aligned according to pattern or fabric nap. The patterns are used to guide a cutting device which slices through the layers with a band or rotary blade. The pieces are then bundled, labeled and sent to a sewing station for assembly by single needle, blind stitch and/or overlock machines, depending upon the seam and fabric. The hook and loop fasteners 42, or their equivalent, will be added during this process and finished garments will be the result.

Whereas, the present invention has been described with respect to a specific embodiment thereof it will be understood that various changes and modifications will be suggested to one skilled in the art, and it is intended to encompass such changes and modifications as fall within the scope of the appended claims. For example, the shield of the present invention could be produced in a range of sizes to fit all users. In addition, the shield could be produced in other shapes to fit arm, leg or lower torso catheters for similar shower protection of those areas.

I claim:

1. A shield for protecting a catheter while a patient is taking a shower bath, comprising:
   first means for engaging a first portion of a patient's body;
   second means for engaging a second portion of the patient's body;
   a waterproof panel spanning between the first and second means and having at least two lateral sides; and
   water absorbent panels attached to the lateral sides of the waterproof panel and spanning between the first and second means.

2. A shield for protecting a catheter while a patient is taking a shower bath, comprising:
   a first band for engaging a first portion of a patient's body and having an intermediate portion;
   a second band for engaging a second portion of the patient's body and having an intermediate portion;
   a waterproof panel spanning between the intermediate portions of the bands; and
   water absorbent panels on lateral sides of the waterproof panel and spanning between the intermediate portions of the bands.

3. A shield for protecting a catheter while a patient is taking a shower bath, comprising:
   a first band for engaging a patient's neck and having an intermediate portion between two ends, and the first band intermediate portion having two lateral edges;
   a second band for engaging a patient's chest and having an intermediate portion between two ends, and the second band intermediate portion having two lateral edges;
   hook and loop fasteners attached to the ends of the bands;
   a waterproof panel having an upper edge, a lower edge and two lateral edges, the waterproof panel spanning between the intermediate portions of the bands, with the upper edge attached to a first band intermediate portion lateral edge and the lower edge attached to the second band intermediate portion lateral edge, the other intermediate portion lateral edges being free edges; and
   water absorbent panels on lateral sides of the waterproof panel, each water absorbent panel having an upper edge, a lower edge and two lateral edges, the water absorbent panels spanning between the intermediate portions of the bands, with the upper edges attached to the first band intermediate portion and the lower edges attached to the second band intermediate portion, and one of the lateral edges of each water absorbent panel attached to one of the waterproof panel lateral edges, with the other lateral edge of each water absorbent panel being a free edge and having elastic to draw the free, lateral edges of the absorbent panels about the patient's body, such that the water proof panel is bounded on all sides by the band intermediate portions and the water absorbent panels.

* * * * *